Figure 2:
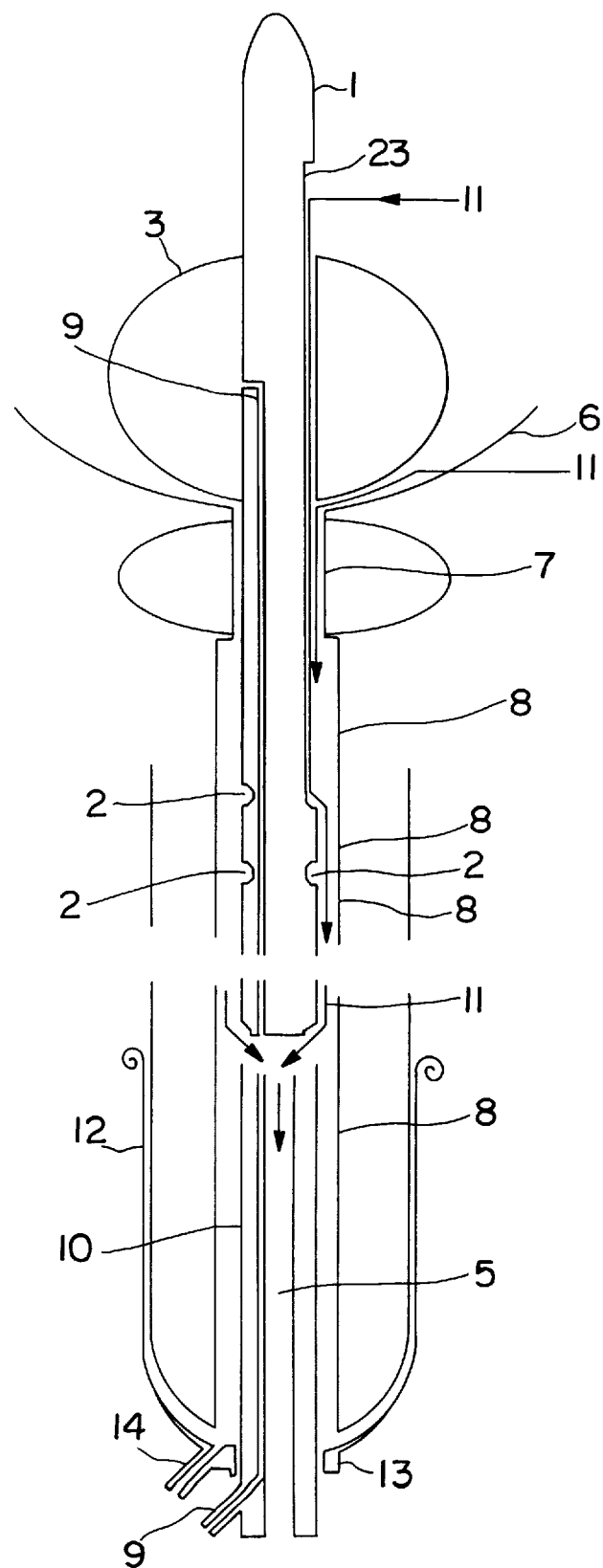
Figure 4A:
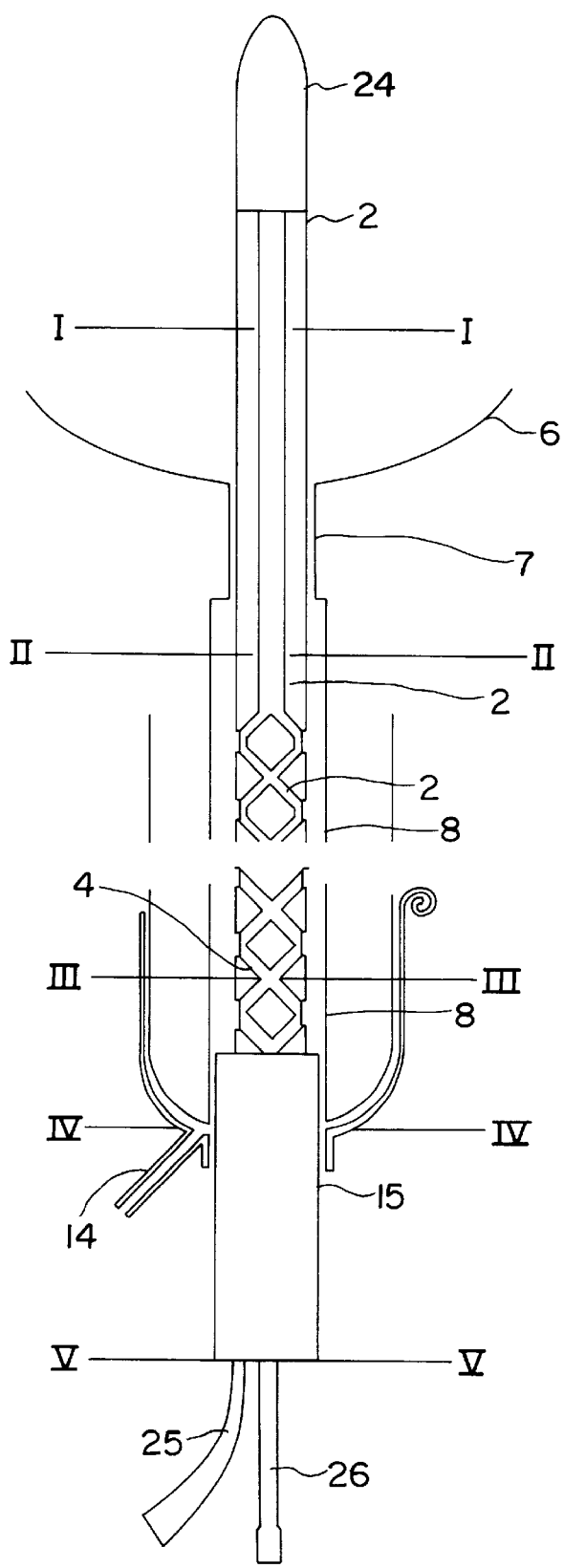
Figure 4B:
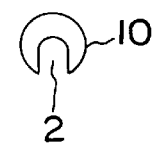
Figure 4C:
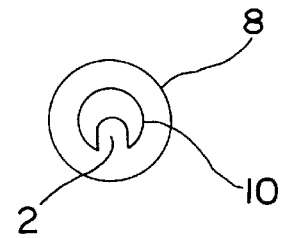
Figure 4D:
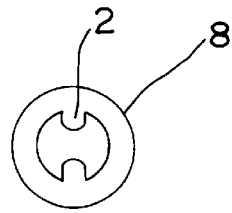
Figure 4E:
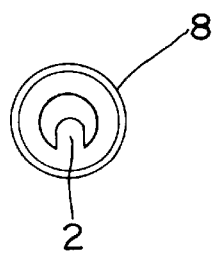
Figure 4F:
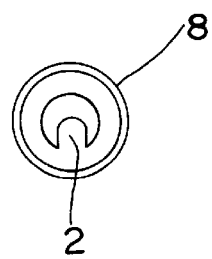

United States Patent [19]
Sachse

[11] Patent Number: 6,080,142
[45] Date of Patent: Jun. 27, 2000

[54] CATHETER WITH GROOVED WALL

[76] Inventor: Hans-Ernest Sachse, Lerchenstrasse 55, 90425 Nuernberg, Germany

[21] Appl. No.: 08/964,315

[22] Filed: Nov. 4, 1997

Related U.S. Application Data

[63] Continuation of application No. 08/510,537, Aug. 2, 1995, abandoned.

[30] Foreign Application Priority Data

Aug. 3, 1994 [DE] Germany ............... 44 27 421

[51] Int. Cl.[7] .................................................. A61M 29/00
[52] U.S. Cl. ..................... 604/544; 604/102; 604/105; 604/326
[58] Field of Search ................. 604/96, 102, 540–544, 604/326, 104–105, 280

[56] References Cited

U.S. PATENT DOCUMENTS 1,661,494  3/1928  Nielsen ................................ 604/174
3,630,206  12/1971 Gingold .
4,249,536  2/1981  Vega ....................................... 604/100
4,579,554  4/1986  Glassman ................................ 604/96
4,627,838  12/1986 Crass et al. ............................ 604/105
4,810,247  3/1989  Glassman ............................... 604/174
4,878,901  11/1989 Sachse ................................... 604/174
4,995,868  2/1991  Brazier .................................. 604/104
5,562,622  10/1996 Tihon .
5,738,654  4/1998  Tihon .

*Primary Examiner*—Mark Bockelman
*Attorney, Agent, or Firm*—Keil & Weinkauf

[57] ABSTRACT

A urethral catheter which irrigates the urethra of the male patient with his own urine to prevent rising urethral infections, wherein the urine flows in groves in the catheter wall between the walls of the catheter and the urethra from the bladder to the mouth of the urethra. In the vicinity of the mouth of the urethra the catheter can be equipped with a condom-like urine collection arrangement. In special cases a metal catheter tip can be held in the bladder by way of a magnet positioned on the belly.

12 Claims, 4 Drawing Sheets

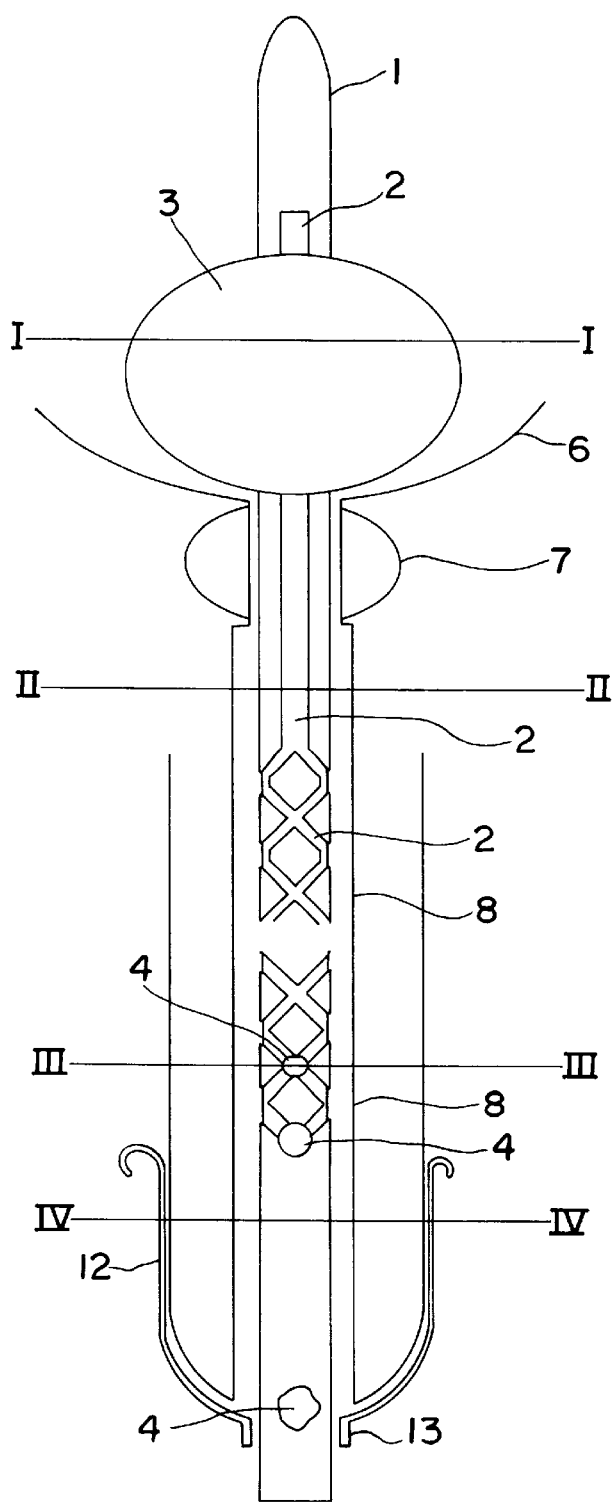
FIG. IA
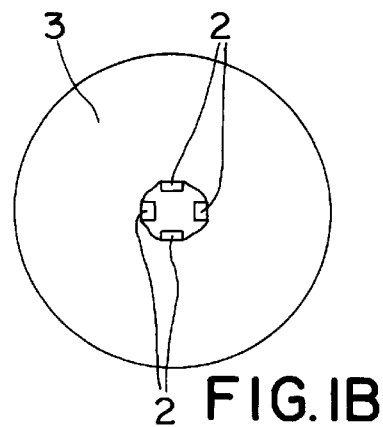
FIG. IB
FIG. IC
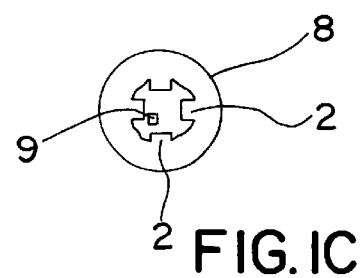
FIG. ID
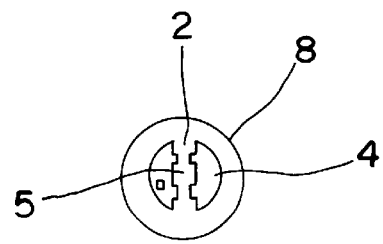
FIG. IE
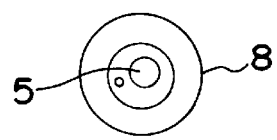

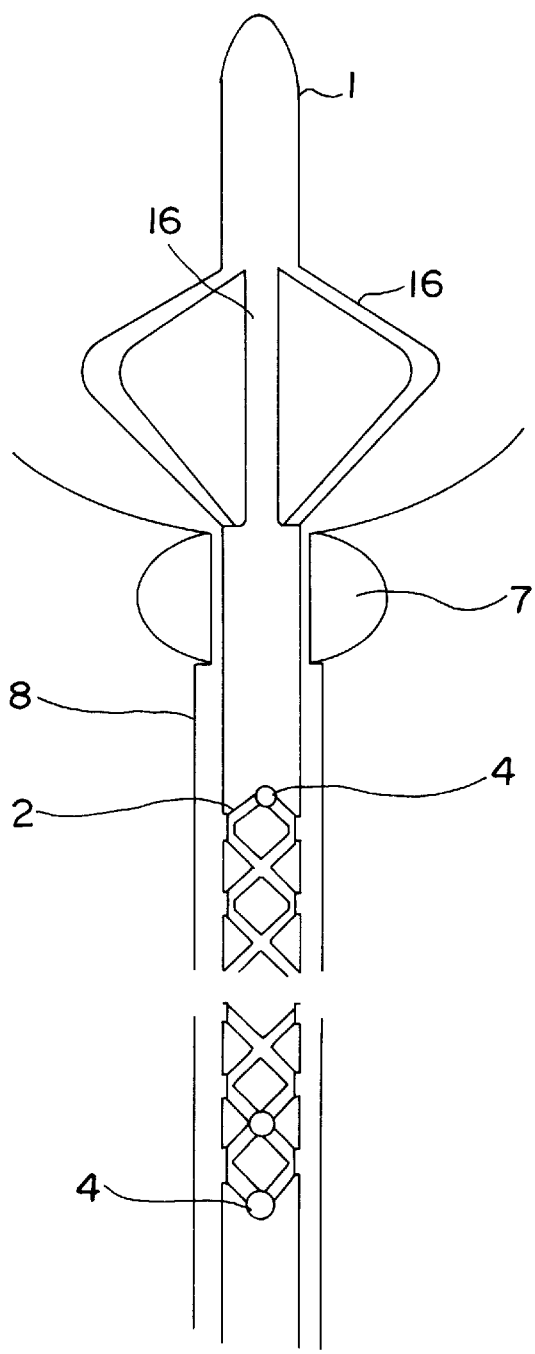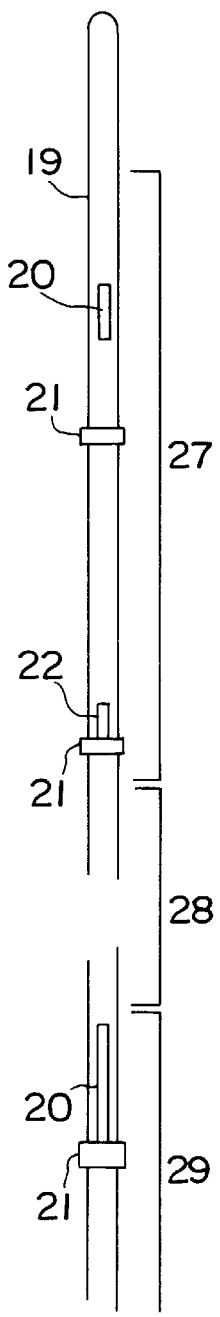
FIG. 3A  FIG. 3B  FIG. 3C

CATHETER WITH GROOVED WALL

This is a Continuation Application of application Ser. No. 08/510,537, filed on Aug. 02, 1995 now abandoned.

This catheter with grooved wall mimics the body's own defense against infection of the urethra. In this catheter the urine flows from the bladder between the walls of the catheter and the urethra, in grooves in the outer wall of the catheter, toward the mouth of the urethra, thereby washing away rising germs.

In one basic embodiment of the invention, just before the mouth of the urethra (described in terms of the direction of the urine flow, i.e. from the bladder toward the mouth of the urethra and thence out of the body) the catheter wall has one or more openings (4), through which the urine still in the urethral area can flow into the catheter lumen (5), whence it can flow into a conventional urine drainage system. The catheter tip (1) is prevented from being expelled from the bladder through familiar mechanisms, in one variation through a balloon or other mechanical restraint, or alternatively through a magnetically restrained metal catheter tip. In order to collect any small quantities of urine that may slip out between the walls of the catheter and the urethra, several embodiments of this invention incorporate condom urinals. Optimal irrigation is achieved by having the grooves arranged variously, for example in a diamond-shaped or spiral pattern.

In another variation the catheter has a lumen that extends from its tip (1) to its opposite end, outside the patient. For greater ease of inserting the catheter into the urethra, an insertion mandrin (17) fits into the lumen, to stiffen the catheter. Furthermore, in this embodiment effective irrigation can be achieved by combining the catheter with an irrigating mandrin (19). The irrigation mandrin (19) is positioned in the lumen in such a way as to force the urine to flow in the grooves, past the mucous membranes of the urethra.

Further features and advantages of the invention are described in the subclaims, as well as in the following description and the drawings. The drawings show:

FIG. 1, A–E a first embodiment in plan view, as well as cross-sectional views at four points FIG. 2 another embodiment in longitudinal cross-section FIG. 3, A–C another embodiment in plan view, alongside an insertion mandrin and an irrigation mandrin in plan view FIG. 4, A–F another embodiment in plan view as well as cross-sectional views of the catheter at five points

FIG. 1

The shaft of the catheter is solid toward its bladder end (cross-sections B and C) and hollow toward its external end (cross-sections D and E), the latter end comprising the lumen (5). Expulsion of the catheter tip (1) from the bladder is prevented by the catheter balloon (3). The catheter balloon inflation channel (9) is located in the catheter shaft and/or the catheter wall and terminates in a not-depicted, conventional inflation tap. The urine from the bladder flows in four grooves (2) to where the grooves split up into diamond-shaped patterns in the urethral area. The urine then flows through the catheter wall openings (4) into the catheter lumen (5) and thence to a not-depicted urine drainage system, in which there is ideally a slight vacuum. Any urine that does not make its way into the lumen (5) and continues to flow between the urethral mucous membranes (8) and the outside of the catheter wall toward the mouth of the urethra is stopped by the condom-like urine collection arrangement. This comprises a condom shaft (12) and a condom sleeve (13), this latter sealed around the catheter shaft, and leads the urine through an opening in the catheter wall (4) located at this spot into the catheter lumen.

FIG. 2

This embodiment corresponds in most regards to FIG. 1, and shows the catheter in longitudinal cross-section. One difference is in the drainage of the condom-like urine collection system. The condom shaft (12), which with the condom sleeve (13) is sealed to the catheter shaft, has its own condom drain tap (14), which is connected to a conventional urine drainage system, which may or may not incorporate a slight vacuum (not depicted).

FIG. 3

This embodiment features a so-called "Casper" basket (16) for preventing expulsion of the catheter tip from the bladder. This rubber or synthetic "Casper" basket, which unfolds by itself due to its innate elasticity, is tensioned and stretched by a stiff insertion mandrin (17) prior to introduction into the body, so that its diameter is reduced to that of the catheter shaft. After the introduction of the catheter and the removal of the insertion mandrin (17) the basket unfolds itself again. As a sign that the catheter tip has reached inside the bladder, urine from the bladder flows through the basket to the insertion mandrin (17) and through the opening (18) into the lumen of the insertion mandrin and through that lumen to the outside. There the appearance of urine shows that the catheter tip has reached the interior of the bladder.

Since, in this embodiment, the urine stream, following the path of least resistance, would "prefer" to flow through the catheter lumen, the removal of the insertion mandrin and its replacement by an irrigation mandrin (19) forces the urine flow into the grooves and between the mucous membranes of the urethra and the outer wall of the catheter. After the positioning of the irrigation mandrin (19) in the catheter lumen, the urine entering through the basket flows through opening 20 into the lumen of the irrigation mandrin. The sleeve 21 seals the wall of the irrigation mandrin (19) against the inner wall of the catheter, although this is not absolutely necessary. The urine flows through the irrigation mandrin's urine conducting section (27) toward the mouth of the urethra. In the area of the urethra the urine flow exits the irrigation mandrin through the urine exit opening (22), downstream from which the lumen of the irrigation mandrin is sealed off. A second sleeve seals the catheter lumen and forces the urine out through the catheter wall opening (4) into the grooves (2). At the end of the irrigation section (28), at the last catheter wall opening (4) toward the mouth of the urethra, the urine flows back toward the irrigation mandrin and enters through the slit-shaped urine entry opening (20) of the irrigation mandrin into the lumen of the irrigation mandrin, and flows through the interior urine conduction section, i.e. in the lumen of the irrigation mandrin, out of the body to a urine drainage system (not shown).

FIG. 4

The catheter shaft in this embodiment is solid throughout its length and has no lumen. The tip (24) is made of magnetizable metal and can, once introduced into the bladder, be held in place by means of a magnet fastened to the belly, thus requiring no mechanical restraint. The urine in the bladder flows into the groove (2) and through the diamond shaped pattern of grooves in the urethral region. In the area of the mouth of the urethra the exit sleeve (15) surrounds the catheter shaft and groove (2). The exit sleeve can then be connected directly to a conventional drainage system.

Index to Reference Numerals 1. catheter tip
2. catheter wall groove
3. balloon
4. catheter wall opening
5. catheter lumen
6. inner wall of the bladder
7. prostate/sphincter region
8. urethral wall/mucous membranes
9. inflation channel for the balloon
10. outer wall of the catheter
11. direction of urine flow
12. condom shaft
13. condom sleeve
14. condom drain tap
15. exit sleeve
16. "Casper" basket
17. insertion mandrin
18. opening in the insertion mandrin
19. irrigation mandrin
20. urine entry opening in the irrigation mandrin
21. sealing sleeve
22. urine exit opening of the irrigation mandrin
23. widened longitudinal groove of the catheter shaft
24. metal catheter tip
25. inflation tap for the inflation channel
26. urine drain tap to the urine drainage system
27. bladder-end urine conducting section of the irrigation mandrin
28. irrigation area of the irrigation mandrin
29. urethral mouth-end urine conducting section of the irrigation mandrin

I claim:

1. A catheter for use in the bladder and urethra having a tip end and an opposite end, and having a catheter shaft extending between the tip end and the opposite end said shaft being solid towards the tip end and having a lumen positioned towards the opposite end, said catheter having grooves extending from the said tip adapted to receive the flow of urine from the bladder in the outer surface of the catheter wall, wherein there are one or more holes in the grooves of the catheter wall leading to the lumen in the catheter whereby the urine flow is directed from the grooves to the interior of the lumen, said holes being located in such a manner that when the catheter is positioned for use in the body, said holes are in the area of the urethra farthest from the bladder.

2. A catheter as defined in claim 1, wherein the tip end of the catheter is adapted for insertion into the bladder and which tip end comprises restraint means for holding the catheter positioned when inserted into the bladder.

3. The catheter as defined in claim 2, wherein the means of restraint is a balloon or a Casper basket.

4. A catheter as defined in claim 1, further comprising a condom-like urine collection arrangement at the opposite end of the catheter adapted for engagement with the tip of the penis comprising a condom shaft and a condom sleeve, said condom sleeve being sealed to the outside of the catheter.

5. A catheter as defined in claim 4, wherein said condom-like urine collection arrangement has its own condom drain tap with its own urine drainage system.

6. A catheter as defined in claim 1, wherein the wall grooves are arranged in diamond-shaped or similar net-like patterns.

7. A catheter as defined in claim 1, wherein the wall grooves are arranged in spiral patterns.

8. A catheter as defined in claim 1, wherein the lumen extends between the tip end and the opposite end, which catheter further comprises an insertion mandrin which insertion mandrin is adapted to be received by the lumen of the catheter.

9. A catheter as defined in claim 8, wherein the insertion mandrin is sufficiently stiff, so that, when the insertion mandrin is inserted into the lumen of the catheter, the insertion mandrin stabilizes the catheter to allow the catheter to easily pass through the urethra.

10. A catheter as defined in claim 8, wherein the insertion mandrin is hollow and has a tip with an opening near it.

11. A catheter as defined in claim 8, further comprising an irrigation mandrin, wherein the irrigation mandrin has a lumen and a wall and is provided with one or more sealing sleeves and openings in the irrigation mandrin wall, which lead to the lumen of the irrigation mandrin, said sleeves and openings being arranged in such a manner that with proper positioning of the irrigation mandrin in the lumen of the catheter the urine stream is lead through the wall grooves of the catheter.

12. A catheter as defined in claim 1, further in combination with a corresponding magnet, wherein the tip end of the catheter is made of magnetizable metal, and said corresponding magnet is adapted to be adhered to the skin of the belly or otherwise fastened near the bladder.

* * * * *